(12) United States Patent
Doherty

(10) Patent No.: US 9,072,560 B2
(45) Date of Patent: Jul. 7, 2015

(54) IMPLANT REMOVAL AID FOR USE WITH IMPLANTS UTILIZING A DATA CARRIER

(75) Inventor: Michael Casey Doherty, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 65 days.

(21) Appl. No.: 13/271,463

(22) Filed: Oct. 12, 2011

(65) Prior Publication Data

US 2013/0092564 A1 Apr. 18, 2013

(51) Int. Cl.
*A61B 17/86* (2006.01)
*A61B 19/00* (2006.01)

(52) U.S. Cl.
CPC .............. *A61B 17/865* (2013.01); *A61B 19/44* (2013.01); *A61B 2019/448* (2013.01)

(58) Field of Classification Search
CPC ............. A61B 19/026; A61B 17/1222; A61B 17/105; B65D 5/5021; B65D 83/0481; B65D 2215/02; B65D 83/0463
USPC .............. 206/339, 368, 369, 370, 438, 459.1, 206/459.5, 562–564; 235/385; 439/180; 606/302
See application file for complete search history.

(56) References Cited

U.S. PATENT DOCUMENTS

| | | | |
|---|---|---|---|
| 4,154,342 A | | 5/1979 | Wallace |
| 4,372,011 A | * | 2/1983 | Aranyos ....................... 24/20 TT |
| 4,553,669 A | | 11/1985 | Butterworth et al. |
| 4,564,163 A | * | 1/1986 | Barnett ........................... 248/71 |
| 4,935,992 A | * | 6/1990 | Due ............................. 24/16 R |
| 5,330,442 A | * | 7/1994 | Green et al. ................... 606/232 |
| 5,400,562 A | * | 3/1995 | Bahr ................................ 52/684 |
| 5,676,254 A | * | 10/1997 | Cheng et al. ................... 206/751 |
| 5,690,223 A | * | 11/1997 | Wood ............................. 206/363 |
| 7,118,029 B2 | | 10/2006 | Nycz et al. |
| 7,213,767 B2 | | 5/2007 | Tethrake et al. |
| 7,256,699 B2 | | 8/2007 | Tethrake et al. |
| 7,268,684 B2 | | 9/2007 | Tethrake et al. |
| 7,362,228 B2 | | 4/2008 | Nycz et al. |
| 7,815,123 B2 | | 10/2010 | Conner et al. |
| 8,074,799 B2 | | 12/2011 | Fujii et al. |
| 8,079,518 B2 | | 12/2011 | Turner et al. |

(Continued)

FOREIGN PATENT DOCUMENTS

EP 2332487 6/2011

OTHER PUBLICATIONS

Orthopedics This Week, vol. 4, Issue 4, p. 4, Feb. 5, 2008, "Radio Frequency Identification and Orthopedics".

*Primary Examiner* — Anthony Stashick
*Assistant Examiner* — Kaushikkumar Desai
(74) *Attorney, Agent, or Firm* — Sorell Lenna & Schmidt LLP

(57) ABSTRACT

A storage system for packaging and storing medical devices with associated data carriers, or tags that can be used for tracking inventory levels and uses of an implant. The storage system includes at least one medical device, and at least one data carrier secured to the at least one medical device, the data carrier including an enlarged substantially planar surface. The storage system further includes a storage device having one or more cavities adapted to receive the medical device and data carrier, each cavity including a cut-out positioned at least partially beneath the enlarged substantially planar surface that allows at least a portion of the enlarged substantially planar surface to pass at least partially there-through.

17 Claims, 5 Drawing Sheets

(56) References Cited

U.S. PATENT DOCUMENTS

| | | |
|---|---|---|
| 8,087,325 B2 | 1/2012 | Neubardt |
| 2005/0033430 A1 | 2/2005 | Powers et al. |
| 2006/0244652 A1 | 11/2006 | Tethrake et al. |
| 2007/0001839 A1 | 1/2007 | Cambre et al. |
| 2007/0095689 A1 | 5/2007 | Pratt et al. |
| 2007/0125392 A1 | 6/2007 | Olson et al. |
| 2007/0144926 A1 | 6/2007 | Bettenhausen et al. |
| 2007/0159337 A1 | 7/2007 | Tethrake et al. |
| 2007/0188306 A1 | 8/2007 | Tethrake et al. |
| 2007/0239289 A1 | 10/2007 | Cambre et al. |
| 2007/0250017 A1* | 10/2007 | Carred et al. ............. 604/220 |
| 2007/0284428 A1 | 12/2007 | Cambre et al. |
| 2008/0230421 A1 | 9/2008 | Pleil et al. |
| 2008/0230422 A1 | 9/2008 | Pleil et al. |
| 2008/0230423 A1* | 9/2008 | Loeffler et al. ............. 206/438 |
| 2008/0282509 A1* | 11/2008 | Fay ............................ 24/19 |

\* cited by examiner

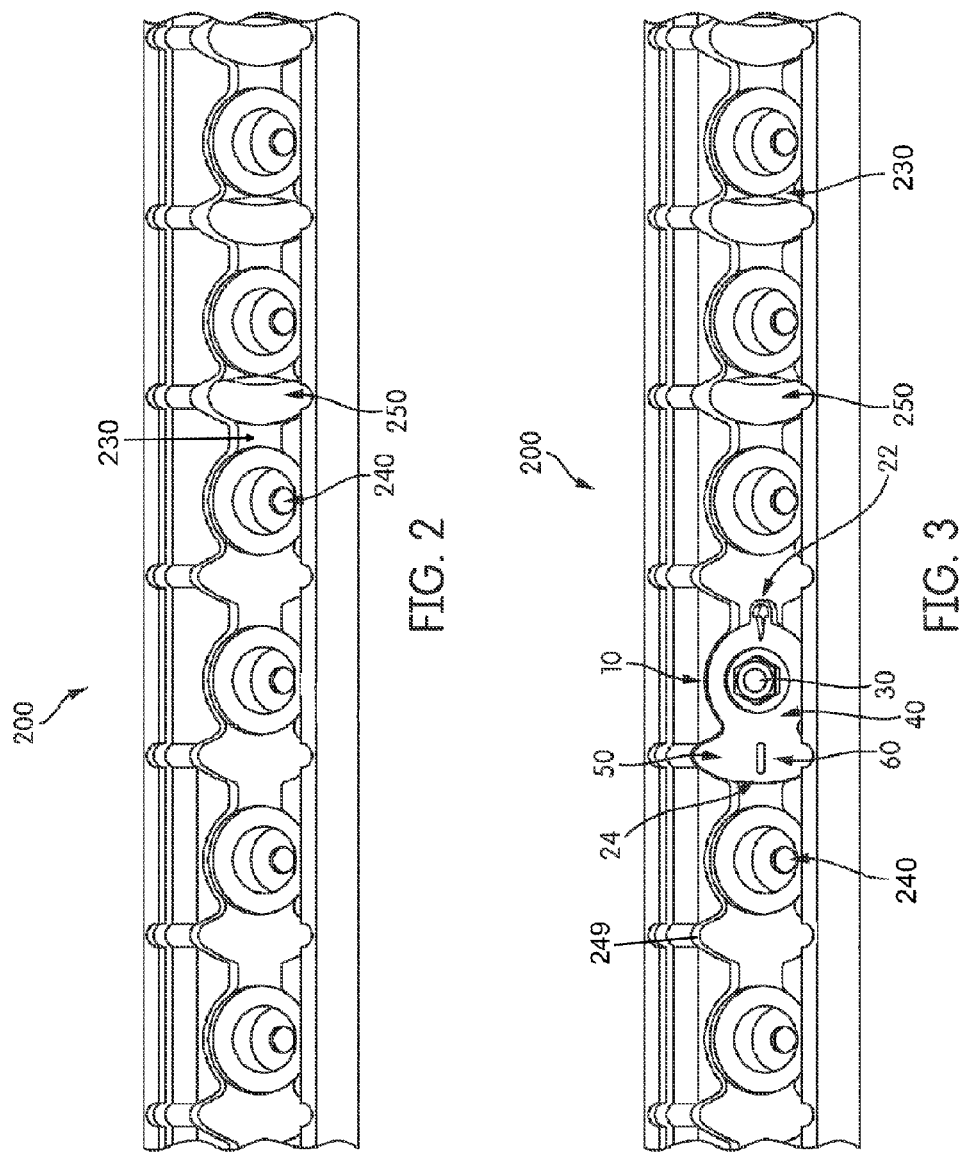

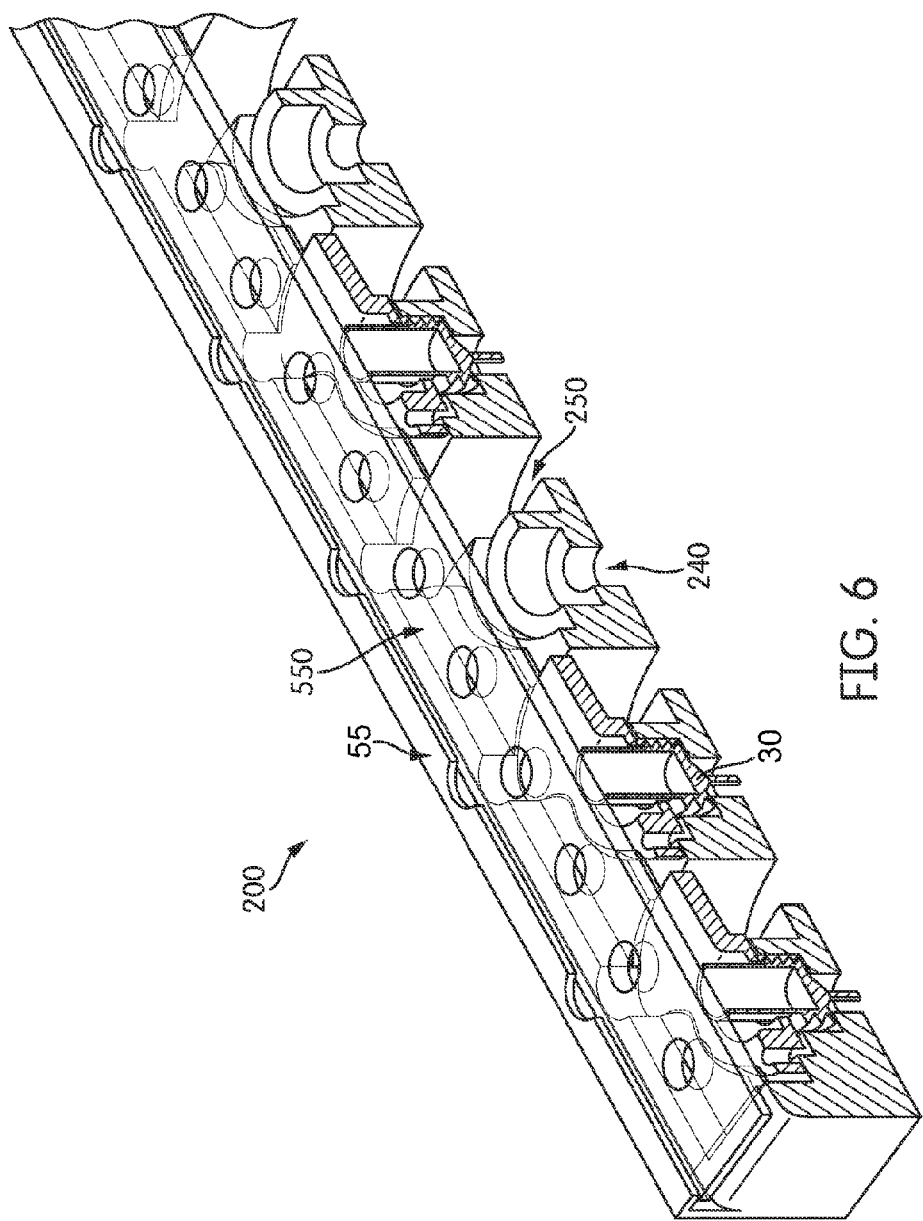

IMPLANT REMOVAL AID FOR USE WITH IMPLANTS UTILIZING A DATA CARRIER

BACKGROUND

There is a need to track medical devices from their base materials and manufacture to their use, and throughout the intervening time. These include sterile and non-sterile medical devices. A non-sterile medical device is a medical device that is shipped from a manufacturer in a condition that is not adequately sterilized for implantation. A sterile medical device is shipped from the manufacture in a condition adequately sterilized for implantation. Healthcare providers may prefer to receive non-sterile medical devices for various reasons. In that regard, because non-sterile devices can be sterilized onsite before a medical procedure, non-sterile medical devices having a longer shelf life than a corresponding sterile medical device. Furthermore, non-sterile medical devices typically are less expensive to package. Additionally, non-sterile medical devices typically can be more densely packaged into a common carrier than sterile devices.

Difficulty arises in tracking these medical devices. For example, some smaller medical devices are difficult to track because medical devices generally do not have adequate surface area for applying marks. Thus, in many instances, medical devices are not tracked beyond their manufacturing facility, and may only be counted when reconciled for payment as one of many products that were not returned to a manufacturer for replenishment.

It is known to place a tag or tags on medical devices that are intended to be implanted into the body. For example, U.S. Patent Application Publication No. 2008/0230423, the disclosure of which is incorporated herein by reference in its entirety, discloses a holding device for an implant, such as a screw or rod to be used in surgery, where the holding device may contain identifying information regarding the implant. Other tags attached to medical devices, particularly small medical devices are disclosed in co-pending U.S. patent application Ser. No. 12/109,517, filed Apr. 25, 2008, U.S. patent application Ser. No. 12/109,534, filed Apr. 25, 2008, U.S. patent application Ser. No. 12/109,539, filed Apr. 25, 2008, and U.S. patent application Ser. No. 12/512,274, filed Jul. 30, 2009, the disclosures of each of which are entirely incorporated herein by reference.

While these tags provide a means for tracking and tracing medical devices, it is not easy to remove the implant and/or tag from their packaging (tray, case, etc.), and often they can only be removed with a tool. This becomes very difficult and cumbersome during surgery. Accordingly, there is a need for a storage case, packaging module, or other implant-tag storage or display device that enables quick and efficient implant removal without the need for specially designed tools.

SUMMARY

Disclosed herein is a medical device storage system for tracking inventory levels and uses of medical devices that enables quick and easy removal of devices that are packaged together with a data carrier (e.g., tag). In accordance with the embodiments, there is provided a medical device storage system comprising at least one medical device, each medical device having secured thereto a data carrier in which the data carrier includes an enlarged substantially planar surface. The system further includes a storage device that includes one or more cavities shaped to receive the medical device and data carrier, each cavity including a cut-out or groove that allows at least a portion of the enlarged substantially planar surface to pass at least partially there-through.

In another exemplary embodiment, a method for removal of a medical device packaged together with a data carrier is provided. The method includes providing a storage device having a longitudinal axis and one or more cavities positioned along the longitudinal axis, the one or more cavities having positioned therein one or more medical devices having secured thereto a data carrier in which the data carrier includes an enlarged substantially planar surface. The one or more cavities include a cut-out or groove that allows at least a portion of the enlarged substantially planar surface to pass at least partially there-through. The method further includes pressing on the substantially planar surface of the data carrier in a direction generally orthogonal to the longitudinal axis of the storage device to push at least a portion of the data carrier at least partially through the cut-out or groove, thereby raising up the opposite side of the data carrier, gripping the opposite side of the carrier, and removing the medical device and data carrier from the storage device.

The system and method provide for easy, manual removal of medical devices packaged together with a data carrier, without the need for a tool or other device to remove the medical device. The system and method also enable an individual to remove the medical device packaged together with a data carrier even if that individual were wearing gloves. The system and method also enable an individual to remove the medical device packaged together with a data carrier without having to deform the data carrier or medical device, for example, without having to squeeze or pinch the data carrier or medical device to un-snap the data carrier from the storage device. These and other aspects, forms, objects, features, and benefits of the present invention will become apparent from the following detailed drawings and description.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

FIG. 2 is a perspective view of a storage device containing a plurality of conventional cavities, and a plurality of cavities in accordance with one embodiment of the present disclosure.

FIG. 3 is a perspective view of the storage device of FIG. 2, in which a medical device attached to a data carrier is positioned in a conventional cavity.

FIG. 6 is a cross-sectional perspective view as shown in FIG. 4, with a retaining member positioned over the plurality of medical devices attached to data carriers.

DETAILED DESCRIPTION

Figure 1:
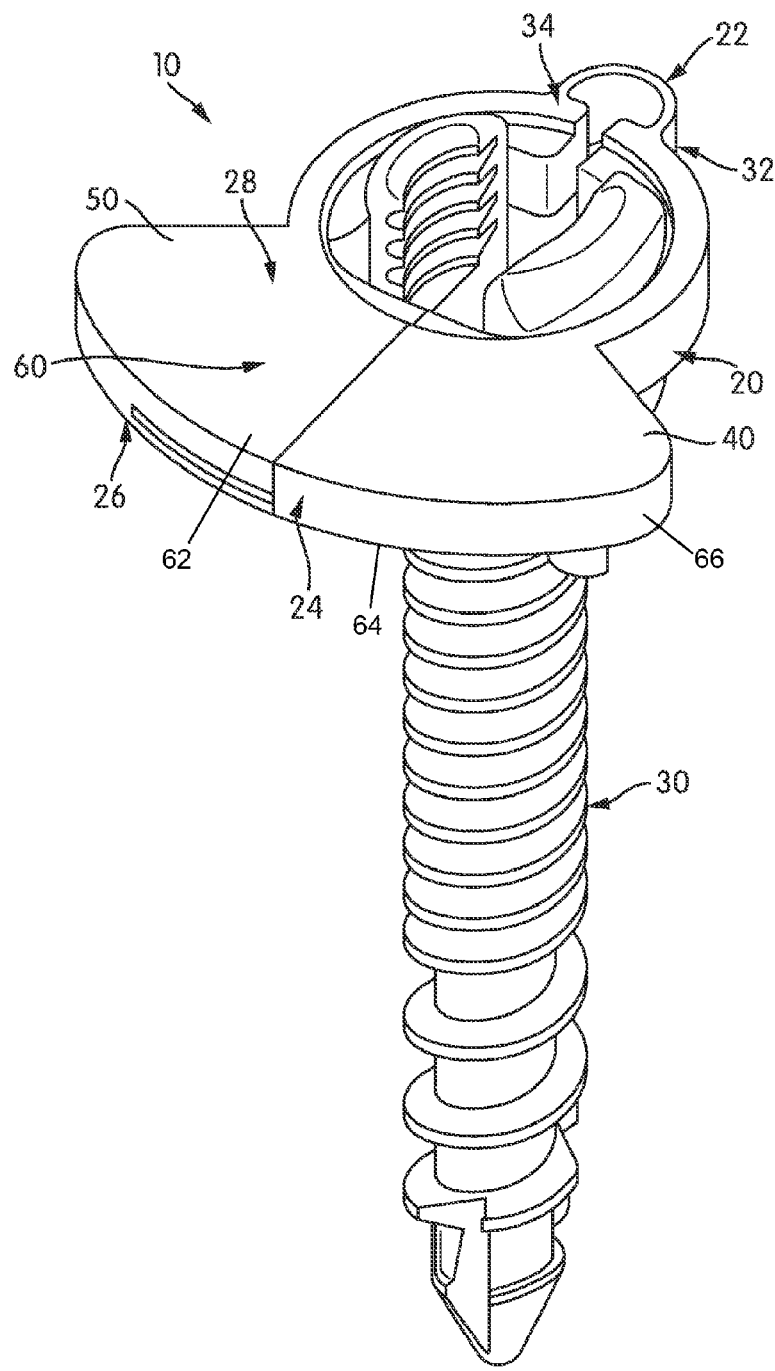
FIG. 1 is a perspective view of a medical device having attached thereto a data carrier according to one embodiment of the present disclosure.

The present disclosure relates generally to the field of orthopedic surgery, and more particularly to devices, systems and methods for tracking and tracing medical devices through the use of removable data carriers or tags. The present disclosure relates more specifically to storage devices (or packaging devices) used to store medical devices associated with a removable data carrier, and to methods of manually removing the medical devices with removable data carrier from the storage device. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

Referring first to FIG. 1, a perspective view of a medical device 30 associated with a data carrier, or tag 20 is shown, in which the combined product is referenced by numeral 10. The data carrier is shown in its locked position with lobes 40 and 50 connected to one another. The medical device 30 can be inserted into the data carrier 20 when lobes 40 and 50 are spread apart, and then the two lobes 40, 50 can be brought into engagement with one another. The lobes 40, 50 remain connected to one another until the medical device 30 is removed, the connection being any connection means, including adhesive, snap fit, mechanical fastening with a screw, nail, rivet, or the like. The data carrier 20 typically is provided with a tamper evident locking mechanism that allows the medical device 30 to be removed upon application of force, such as twisting the data carrier 20, or snapping lobes 40, 50 in opposing directions along longitudinal axis LB.

The data carrier 20 includes a distal portion 22 and proximal portion 24, although their relationship as distal and proximal can be reversed. Distal portion includes opposing surfaces 32, 34, and the proximal portion includes opposing surfaces 26, 28. Data carrier 20 also includes an enlarged substantially planar portion 60, which as shown in FIG. 1 is essentially a combination of lobes 40 and 50. As shown in FIG. 1, enlarged substantially planar portion 60 includes a top surface 62 and a bottom surface 64 opposite top surface 62. As shown in FIG. 1, enlarged substantially planar portion 60 includes a side surface 66 that extends transverse to top surface 62 and bottom surface 64. Side surface 66 extends continuously between top and bottom surfaces 62, 64 to connect top surface 62 with bottom surface 64. Enlarged substantially planar portion 60 may include indicia that represent markings or tracking devices capable of retaining identifying information, for example, relevant to the medical device 30 captured by data carrier 20. Additionally, the indicia may represent identifying information related to the patient receiving the device, medical procedure used with the device, manufacturing information such as materials, processes, customer/supplier, and lot information of similarly manufactured devices. The identifying information is not intended to be limiting in scope by this disclosure, but instead is presented for exemplarily purposes only. Furthermore, any required manufacturing standards requiring the marking of products with certain identifying information is considered to be within the scope of identifying information capable of be represented by the indicia. Therefore, there is no need for the medical device 30 captured by data carrier 20 to have identifying information because the data carrier 20 provides any necessary identifying information.

In the embodiment shown in FIG. 1, the indicia represent a two dimensional bar code and alphanumeric lettering, respectively used to identify the medical device 30 captured by data carrier 20. However, the indicia, or any tracking device herein, may be any device that is capable of retaining identifying information. For example, the indicia can be a one or two dimensional barcode capable of being scanned by an optical scanner. Such an optical scanner may include a barcode scanner made by Baracoda such as the Evolution scanner (part number: B40160202).

Additionally, the tracking device or indicia may be in the form of a radio frequency identification (RFID) device built into the lobes 40, 50 of data carrier 20, or built into any other portion of data carrier 20. Such an RFID device can transmit a radio frequency signal to an RFID transceiver that can obtain the identifying information of the medical device stored in the RFID device. Additionally, the indicia can include, for example, human readable information and/or data that may include visual alphanumeric characters and tactile features such as different surface textures and/or raised or lowered portions. Furthermore, the data carrier 20 can include a sealable groove, slot, or compartment (not shown) that has a transparent cover such that any human and/or computer readable information can be placed into the sealable groove, slot, or compartment, but can still be read through upper planar surface 28. In addition, the indicia may include a printed adhesive label in either human and/or computer readable form that is resistant to degradation during sterilization procedures.

Furthermore, although the indicia are shown as two separate types of tracking devices, the identifying information contained within these indicia may contain the same amount of identifying information. However, it is also possible that one indicia may provide more identifying information than the other indicia. Additionally, there may be only one indicia on either lobe 40 or lobe 50, but not the other lobe. Furthermore, the same type of indicia may be represented on both lobes 40 and 50. Even more, lobes 40 and 50 may have only one indicia that spans consecutively across the enlarged substantially planar portion 60.

The embodiment shown in FIG. 1 is just one of many types of data carriers or tags that are capable of capturing a medical device, and more specifically a small device onto which identifying information typically is difficult to apply. For example, the data carrier may be similar to that shown in U.S. Patent Application Publication No. 2008/0230423 (the "'423 publication"). The data carrier described in the '423 publication provides for engagement with a storage device or other carrying or packing device, by use of a deformable snap fit engagement. The implant can be removed from the data carrier by use of a tool. The present embodiments represent an improvement over the storage device described in the '423 publication by providing a cut-out, or groove in the cavity into which the implant and data carrier are positioned so that the implant and data carrier can be manually removed readily and easily without the need of a tool. Other data carriers encapsulating implants are disclosed in, for example, U.S. patent application Ser. No. 12/109,517, filed Apr. 25, 2008, U.S. patent application Ser. No. 12/109,534, filed Apr. 25, 2008, U.S. patent application Ser. No. 12/109,539, filed Apr. 25, 2008, and U.S. patent application Ser. No. 12/512,274, filed Jul. 30, 2009, and U.S. patent application Ser. No. 13/281,109, entitled: "Encapsulated Data Carrier Tag for Track and Trace Purposes,", the disclosures of each of which are entirely incorporated herein by reference. Any of the aforementioned data carriers can be used in accordance with the embodiments described herein.

As stated above, data carrier 20 preferably includes a tamper evident locking mechanism so that data carrier 20 can be attached to and removed from a medical device 30 with no component of data carrier 20 remaining permanently attached to the medical device 30. Furthermore, it is preferred that there are no loose portions or particulates of data carrier 20 that separate from the data carrier upon unlocking the tamper evident locking mechanism. Therefore, the tamper evident locking mechanism allows data carrier 20 to be attached to a medical device 30 as a one-piece tag and be separated from the medical device as a one-piece tag.

The data carriers disclosed herein are only temporarily attached to the medical device and are utilized for tracking the use of and associated inventory levels of the medical devices. In that regard, prior to use of a medical device having such a data carrier, the data carrier is inspected for detectable evidence of the tamper evident locking mechanism being broken and/or the data carrier being removed from the medical device. If there are no signs of the data carrier being removed from the implant and/or the tamper evident locking mechanism being broken, then a healthcare provider can remove the data carrier from the implant by breaking the tamper evident locking mechanism thereby releasing the medical device from the data carrier. If there are signs that the tamper evident locking mechanism has been tampered with and/or other evidence that the data carrier may have been removed from the medical device then the healthcare provider may elect not to use the medical device.

Prior to use of the medical device the data carriers are capable of having indicia readable by a computer. The computer readable indicia, such as a two dimensional barcode or RFID stored data can be scanned to create a label containing the identifying information relating to the medical device captured by the data carrier. In the event that a data carrier cannot be scanned, the human readable indicia on the data carrier can be utilized to create the label. Subsequently, the label may be attached to a patient's medical chart. Thereafter, the data carrier is discarded after the corresponding label has printed, or placed in a used container or tray to verify the position in which the medical device was implanted (e.g., which bone contains the implant, or what tissue contains the implant, and where is that bone or tissue on the body). In this manner the data carriers can be utilized to track implant use and associated inventory levels.

Referring to FIG. 2, a perspective view of a storage device or packaging 200 for storing and retaining data carriers and their associated medical devices during transport and handling for attachment is shown. The storage device 200 shown in FIG. 2 contains a plurality of cavities having a shape corresponding substantially to the shape of the data carrier and associated medical device. FIG. 2 illustrates a plurality of cavities 230 in accordance with an exemplary embodiment.

The storage device 200 shown in FIG. 2 has a longitudinal axis extending along the length thereof (shown as L1 in FIG. 4), and is depicted as a generally rectangular sleeve. The storage device 200, however, can be of any shape and size, including circular, rectangular, square, and one or more storage devices may be packaged together as a set, or together with other larger implants in a surgical tray, for example. The storage device 200 also may include only one cavity, or a plurality of cavities of the same size and shape, or of varying sizes and shapes to accommodate various sized data carriers and medical devices. The storage device 200 depicted in FIG. 2 is shown merely for purposes of illustrating the preferred embodiments.

Cavity 230 would be designed so that the data carrier and associated medical device fit in snugly, or even snap fit as described in the '423 publication, thereby securing the data carrier and associated medical device to the storage device 200. This prevents the data carrier and medical device from being dislodged during transport, handling, and sterilization, as would be appreciated by those having ordinary skill in the art. Cavity 240 in accordance with an exemplary embodiment described herein also is depicted in FIG. 3. As shown, cavity 230 includes a conventional cavity 240 and a cut-out, or groove 250 into which the enlarged substantially planar portion 60 of data carrier 20 rests. FIG. 2 shows cut-out 250 passing through the entire storage device 200, although cut-out can be recessed into the storage device in an amount that permits the enlarged substantially planar portion 60 to be pressed in a direction substantially orthogonal to the longitudinal axis L1 (in the direction of A1 in FIG. 4, or along axis L3) so that the opposing surface of data carrier 20 will be raised up (in the direction of A2 in FIG. 4) enough to allow an individual's finger to be placed underneath the data carrier 20, to then remove the data carrier 20 from storage device 200. As shown in FIG. 3, cut-out 250 is defined by an inner surface 249 of storage device 200. Data carrier 20 may be positioned within cut-out 250 such that side surface 66 of enlarged substantially planar portion 60 engages inner surface 249, as shown in FIG. 3.

FIG. 3 depicts a perspective view of a storage device 200 for storing and retaining at least one data carrier and associated medical device 10 during transport and handling. The storage device 200 of FIG. 3 includes at least one data carrier and associated medical device 10 in cavity 230. As shown, the data carrier and associated medical device 10 is seated within cavity 230. Enlarged substantially planar portion 60 therefore cannot be pressed down in a direction substantially orthogonal to the longitudinal axis of storage device 200 in any appreciable amount to lower proximal portion 24 and raise distal portion 22 in an amount sufficient to enable an individual to grasp distal portion 22. Accordingly, a tool would be required to either pry data carrier and associated medical device 10 from cavity 230, or to engage with medical device 30 to remove the data carrier and associated medical device 10 from storage device 200. Thus, the present embodiments represent an improvement over the arrangement shown in FIG. 3, as will be described in more detail below with reference to FIG. 4.

Figure 4:
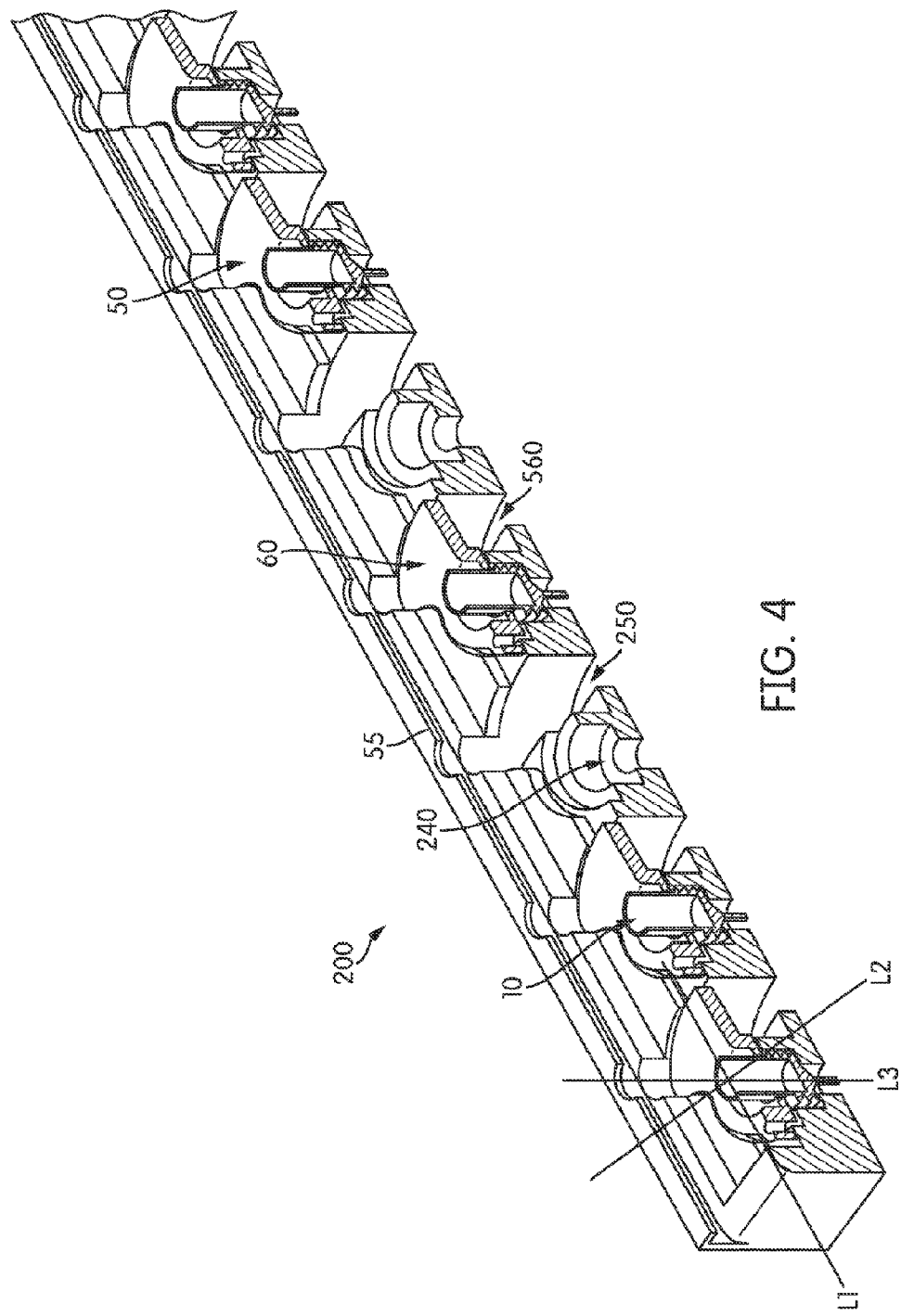
FIG. 4 is a cross-sectional perspective view of a storage device in accordance with an embodiment of the invention in which a plurality of medical devices attached to data carriers are positioned in cavities having cut-outs to enable their easy removal.

FIG. 4 depicts a perspective view of a storage device 200 for storing and retaining at least one data carrier and associated medical device 10 during transport and handling. The storage device 200 of FIG. 4 includes a plurality of data carriers and associated medical devices 10 in a cavity 230 in accordance with the preferred embodiments. As shown, the data carrier and associated medical device 10 is seated within cavity 230 with lobe 50 positioned above cut-out or groove 250 of cavity 230 (lobe 40 has been cut-away in the cross-sectional view shown in FIG. 4). Enlarged substantially planar portion 60 therefore can be pressed down in a direction substantially orthogonal to the longitudinal axis L1 of storage device 200 (along axis L3) to lower proximal portion 24 (in the direction of A1) and raise distal portion 22 (in the direction of A2) in an amount sufficient to enable an individual to grasp distal portion 22. Accordingly, a tool is not required to remove the data carrier and associated medical device 10 from storage device 200.

Figure 5:
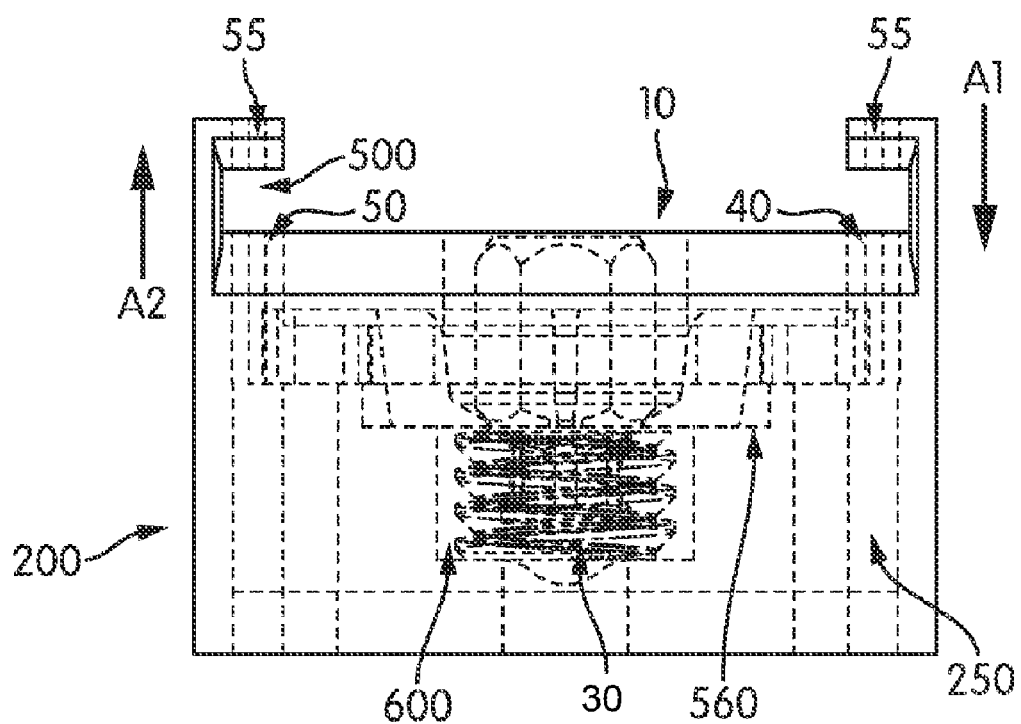
FIG. 5 is a cross-sectional view of a storage device along longitudinal axis L1 of FIG. 4.

In an alternative embodiment, cavity 230 in storage device 200 also preferably includes at least one nub or upper ledge 55 (two upper ledges 55 are shown in FIG. 5 positioned adjacent to the lateral edges of lobes 40 and 50) that secure data carrier and associated medical device 10 into position and prevent it from falling out of storage device 200, even if turned upside down. Cut-out or groove 250 also may be provided with at least one flange, and preferably a mating flange on the other site of cut-out 250 that prevents movement of data carrier and associated medical device 10 in the direction of A1, thus preventing it from falling through the cut-out 250. Referring to FIGS. 4 and 5, the method of inserting the data carrier and associated medical device 10 into storage device 200, as well as its removal, can more readily be seen.

To insert the data carrier and associated medical device 10, the item is angled slightly on its side so that, for example, lobe 50 is raised in the direction of A2 and lobe 40 can be placed under upper ledge 55 so that it approaches or even touches the flange, if present, near the bottom of cut-out 250. Cavity 230 should be designed of sufficient thickness so that lobe 50 then can be rotated back so that it is somewhat level with lobe 40 and positioned under upper ledge 55 on the opposing lateral side of cavity 240. Data carrier and associated medical device 10 now are in their storage and transport position.

In this alternative embodiment, removal of data carrier and associated medical device 10 then preferably may be accomplished as described above. That is, enlarged substantially planar surface 60 is pressed near proximal portion 24 in direction of A1, so that distal portion 22 is raised in the direction of A2 in an amount sufficient to enable a user to grasp distal portion 22. The user then can slightly rotate data carrier and associated medical device 10 in either direction (e.g., either lobe 50 moving in the direction of A1 or lobe 40 moving in the direction of A1), and the entire package removed from cavity 240.

Removal of data carrier and associated medical device 10 from cavity 230 is made even more readily and easily by ensuring that cavity 230 is of sufficient size to seat medical device 30, and provide additional room for medical device 30 to move. FIG. 5 depicts a space 600 surrounding medical device 30 to provide additional room for the data carrier and associated medical device 10 to pivot about a pivot point on ledge 560 so that the item can be removed from storage device 200. While the space 600 is illustrated as an annular space surrounding medical device 30 (a cylindrical screw), those skilled in the art will appreciate that space 600 can be of any suitable shape, depending on the shape and size of medical device 30. The cross-sectional view of FIG. 4 illustrates how ledge 560 functions as a pivot point upon which the data carrier and associated medical device 10 can pivot in the direction of A1 when enlarged substantially planar portion 60 is pressed into cavity 250.

FIGS. 5 and 6 also illustrate an alternative embodiment for securing data carrier and associated medical device 10 within cavity 230. FIG. 5 illustrates a space 500 formed between upper ledges 55 and the opposing lobes (40, 50) of data carrier and associated medical device 10. To secure the plurality of data carriers and associated medical devices 10 within storage device 200, a retaining sleeve 550 can be placed within space 500. Retaining sleeve 550 is shown in shadow in FIG. 6 as covering only a portion of the data carriers and associated medical devices 10, which is preferred. Those skilled in the art will appreciate that retaining sleeve 550 could cover all or even less of the data carriers and associated medical devices 10 than that depicted in the preferred embodiment of FIG. 6. Preferably, retaining sleeve 550 is transparent to provide a clear view of the data carriers and associated medical devices 10 positioned with storage device 200. Removing the data carriers and associated medical devices 10 from storage device 10, in this alternative embodiment, requires sliding retaining sleeve 500 sufficiently away from the item to be removed, and then removing the data carrier and associated medical device 10 as described above.

It should be noted the tamper evident locking mechanism for locking the lobes 40 and 50 discussed above may be accomplished, without limitation, by applying adhesive between the components. Additionally, the tamper evident locking mechanism for locking lobes 40 and 50 discussed above may be accomplished, without limitation, by providing a ratcheting or snap-fit connection between the components that is designed to fracture before other portions of the data carrier when stressed. Furthermore, the tamper evident locking mechanism for locking the lobes 40 and 50 discussed above may be accomplished, without limitation, by melting, welding, ultrasonic welding or otherwise joining all or a portion of the components together.

Furthermore, the tamper evident locking mechanism for locking the lobes 40 and 50 discussed above may include an indicator device across a joint between or through the components that fracture, change shape, change color, or otherwise are altered by separation of the lobes 40 and 50. Detectable separation of lobes 40 and 50 may occur at one or more connections between the components, or may include facture or change within either or both of the lobes 40 and 50, or elsewhere within the data carrier 20.

The data carriers 20 disclosed herein in whole or in part may be constructed of biocompatible materials of various types including metals or polymers. For example, the data carriers 20 may be made in whole or in part of a polymer known as Radel R. In such a scenario, a data carrier 20 is formed in whole or in part using Radel R polymer mixed with barium sulfate ($BaSO_4$). In this manner, the data carrier is radiopaque such that incase of accidental implantation the data carrier can be located via an x-ray, for example. Further, examples of data carrier materials include, but are not limited to, non-cobalt-chromium alloys, titanium alloys, nickel titanium alloys, and/or stainless steel alloys, plastics and polymers including without limitation any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Similarly, storage device 200 may be fabricated in whole or in part from any suitable metal or polymer. Preferably, the storage device 200 is fabricated of a material that can withstand the rigors of sterilization using either a gas or a liquid. Suitable materials that can be used to construct storage device 200, include, but are not limited to non-cobalt-chromium alloys. titanium alloys, nickel titanium alloys, and/or stainless steel alloys, plastics and polymers including without limitation any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE, and mixtures thereof. Particularly preferred materials include Radel® polymers, aluminum, stainless steel, Polypropylux®, Techapro®, Delrin® resin, Ultem® resin, and mixtures thereof.

Although the data carriers 20 described herein are used to track and trace a bone screw 30, this is no way implies a limitation of such medical devices the data carriers can be associated with and used to track. The medical device capable of being tracked by the data carriers described herein may be any implant or instrument used in a medical procedure. In that regard, the medical device of some embodiments may be, without limitation, a surgical screw of any variety, a spinal or other orthopedic plate, a surgical rod, an interbody spinal device, a vertebral disc arthroplasty device, a nucleus replacement device, a corpectomy device, a vertebrectomy device, a mesh device, a facet fixation or arthroplasty device, a structural bone graft, a staple, a tether of synthetic material or wire, or other spinal fixation instrumentation, an intramedullary nail, an external fixation device, a hip prosthesis or therapeutic device, a knee prosthesis or therapeutic device, or an instrument useful with any of the previously recited devices.

The data carrier and indicia 20, storage device 200 and medical devices 30 described herein are capable of undergoing one or more steam sterilization cycles, or other sterilization procedures such as radiation or gas sterilization, without degrading in a manner that would make the data carrier 20 unusable and the device 30 unsuitable for use in a medical procedure. Therefore, the medical devices 30 can be shipped non-sterilized from the manufacture to a healthcare provider, but the non-sterile medical device 30 can still be tracked for inventory purposes and uses thereof through the use of the data carriers 20 and storage devices 200 described herein. The storage device 200 provides a reliable, quick, and easy mechanism for removing the data carrier and associated medical device 10 there from, thus eliminating the need for a tool or device other than an individual's manual manipulation.

The medical device 30 of this or any other embodiment of the invention may consist of materials, by way of example, and without limitation, including titanium and its alloys, ASTM material, cobalt chrome, tantalum, ceramic, polyether-ether-ketone (PEEK), PEAK, various plastics, plastic composites, carbon fiber composites, coral, allograft, autograft, zenograft, and can include artificial materials which are at least in part bioresorbable, or any material suitable for human implantation.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of, the applicant's general or inventive concept. It is understood that all spatial references, such as "longitudinal axis," "horizontal," "vertical," "top," "upper," "lower," "bottom," "left," and "right," are for illustrative purposes only and can be varied within the scope of the disclosure.

What is claimed is:

1. A medical device storage system comprising:
    at least one medical device;
    at least one data carrier comprising a proximal end and a distal end including a distal portion, the data carrier including an enlarged substantially planar portion at the proximal end and a wall defining an opening, the substantially planar portion comprising opposite top and bottom surfaces that are connected by a side surface of the substantially planar portion, the substantially planar portion comprising a first lobe and a second lobe that are connected to each other at the distal portion, planar end surfaces of the first and second lobes engage one another, the at least one medical device being disposed in the opening such that the wall and the distal portion define an enclosure that extends completely around a proximal portion of the at least one medical device;
    a storage device comprising one or more cavities, the medical device being received in one of the cavities, the storage device including a ledge and an inner surface defining a cut-out extending through opposite top and bottom surfaces of the storage device, the data carrier being received in the cut-out such that the side surface engages the inner surface,
    wherein pushing one side of the data carrier through the cutout causes the data carrier to pivot against the ledge such that an opposite side of the data carrier rises up to allow the data carrier to be released from the storage device.

2. The medical device storage system as claimed in claim 1, wherein the first and second lobes are brought together to provide a tamper evident locking mechanism.

3. The medical device storage system as claimed in claim 2, wherein removal of the medical device from the data carrier, after the medical device is secured to the data carrier by the mating engagement of first and second lobes requires breaking the first lobe from the second lobe.

4. The medical device storage system as claimed in claim 1, wherein the one or more cavities comprises a ledge that enables the medical device and data carrier to pivot on the ledge as the enlarged substantially planar portion is pressed into the cut-out.

5. The medical device storage system as claimed in claim 1, wherein the cavity is larger than the medical device positioned within the cavity, thereby providing a space that allows the medical device to move slightly during insertion and removal from the storage device.

6. The medical device storage system as claimed in claim 1, wherein the cavity includes at least one upper ledge that extends at least partially over the enlarged substantially planar portion.

7. The medical device storage system as claimed in claim 6, wherein the at least one upper ledge forms a space between the upper ledge and the top surface of the enlarged substantially planar portion.

8. The medical device storage system as claimed in claim 7, further comprising a retaining sleeve positioned within the space, wherein the retaining sleeve at least partially covers the enlarged substantially planar portion.

9. The medical device storage system as claimed in claim 8, wherein the retaining sleeve is transparent.

10. The medical device storage system as claimed in claim 1, wherein the medical device is selected from the group consisting of a surgical screw, a spinal plate, an orthopedic plate, a surgical rod, an interbody spinal device, a vertebral disc arthroplasty device, a nucleus replacement device, a corpectomy device, a vertebrectomy device, a mesh device, a facet fixation or arthroplasty device, a structural bone graft, a staple, a tether of synthetic material or wire, an intramedullary nail, an external fixation device, a hip prosthesis, a knee prosthesis, and mixtures thereof.

11. The medical device as claimed in claim 1, wherein the enlarged substantially planar portion includes indicia that represent markings or tracking devices capable of retaining identifying information relevant to the medical device.

12. The medical device as claimed in claim 11, wherein the indicia comprises an RFID tracking device.

13. The medical device as claimed in claim 1, wherein the data carrier comprises a tamper evident locking mechanism.

14. The medical device storage system as claimed in claim 1, wherein the distal portion defines a second opening that is separated from the opening by a gap.

15. The medical device storage system as claimed in claim 1, wherein the data carrier is monolithic.

16. The medical device storage system as claimed in claim 1, wherein the data carrier comprises a polyphenylsulfone resin.

17. The medical device storage system as claimed in claim 1, wherein the distal portion defines a void being in communication with the opening.

* * * * *